United States Patent [19]

Johansson et al.

[11] Patent Number: 4,546,085

[45] Date of Patent: Oct. 8, 1985

[54] CELL CULTIVATION CONTAINER

[75] Inventors: Arne Johansson, Roskilde; Sven Ajslev, Kirke Hyllinge, both of Denmark

[73] Assignee: A/S Nunc, Roskilde, Denmark

[21] Appl. No.: 441,615

[22] Filed: Nov. 15, 1982

[30] Foreign Application Priority Data

Nov. 16, 1981 [DK] Denmark ........................... 5076/81

[51] Int. Cl.⁴ ........................ C12M 3/00; C12M 1/00; C12M 1/24; C12M 1/04; B65D 51/16; B01L 3/00

[52] U.S. Cl. .................................... 435/284; 435/287; 435/296; 435/313; 422/102; 215/307

[58] Field of Search ............... 435/284, 296, 298, 299, 435/300, 301, 313, 809, 810; 422/102, 103; 215/31, 307, 329, 341; 220/303, 305, 366

[56] References Cited

U.S. PATENT DOCUMENTS

| | | | |
|---|---|---|---|
| 3,297,184 | 1/1967 | Andelin | 215/307 |
| 3,822,027 | 7/1974 | Cnerba | 215/206 |
| 4,053,078 | 10/1977 | Herr | 215/222 |
| 4,289,248 | 9/1981 | Lynn | 215/330 |

FOREIGN PATENT DOCUMENTS

| | | | |
|---|---|---|---|
| 1417152 | 12/1975 | United Kingdom | 215/222 |
| 2096981 | 10/1982 | United Kingdom | 215/222 |

*Primary Examiner*—Thomas G. Wiseman
*Assistant Examiner*—Jayme A. Huleatt
*Attorney, Agent, or Firm*—Watson, Cole, Grindle & Watson

[57] ABSTRACT

A cell cultivation container with screw cover, where the zone of the mouth portion of the container adjacent the edge of the mouth has a greater diameter than the more remote zone and is constructed with at least two inwardly protruding, axially extending projections, and where the screw cover has an inner skirt with an outer annular bead which in the fully closed position of the cover is in sealing engagement with the inner wall of the narrow zone of the mouth portion of the container, while in partly unscrewed position of the cover the bead is only in contact with the inwardly protruding, axially extending projections. Hereby the cross-sectional area of the communication passages between the interior of the container and the surroundings formed by partial unscrewing of the cover will remain constant, even if the angle of turning of the screw cover varies within wide limits.

2 Claims, 3 Drawing Figures

CELL CULTIVATION CONTAINER

BACKGROUND OF THE INVENTION

The invention relates to a cell cultivation container having a mouth portion provided with a screw cover.

In the growing of cells it is customary to use containers provided with an airtight screw cover in order to prevent contamination of the cell material and also to prevent the escape of cells or substrate to the surroundings.

However, the use of such airtight screw covers involves various practical problems. Thus, an equalization must be performed from time to time of the overpressure building up in the cultivation container, i.e. because the temperature in the container is increased from that of the surroundings to the optimum temperature of about 37° C. for the cultivation of the cells. The overpressure is mainly due to the fact that the gas mixture present above the substrate tends to expand at the noted temperature increase.

In cell cultivation containers a $NaHCO_3$-solution is frequently used for maintaining a constant pH-value. Typically, a $NaHCO_3$-solution is used having a $NaHCO_3$-content of 0.8–3.5 g/l, preferably about 2.2 g/l. Such a buffer solution gives the desired pH-value only if a given $CO_2$ partial pressure above the substrate is maintained, and it is therefore necessary to introduce $CO_2$ into the cultivation container from time to time.

The equalization of the above-mentioned overpressure and the introduction of $CO_2$ into the container are normally performed by turning the screw cover sufficiently to establish a communication between the interior of the container and a surrounding gas mixture, such as atmospheric air with an addition of 5% $CO_2$. However, in the case of the known screw covers it is not possible to ascertain exactly when the cover has been sufficiently opened to establish such communication, yet not opened to such an extent that material may unintentionally escape from the container, or contaminating matter, including micro-organisms, may penetrate into the container.

SUMMARY OF THE INVENTION

It is the object of the invention to provide a cell cultivation container of the kind referred to, which is so constructed such that when the screw cover is turned in the opening direction a predetermined opening of the container is obtained, even if the angle of turning varies within certain limits.

According to the invention, there is provided a cell cultivation container having a mouth portion provided with a screw cover, the zone of the mouth portion adjacent the edge of the mouth having a greater inner diameter than the remaining zone of the mouth portion, two or more inwardly protruding, axially extending projections being provided in the first mentioned zone of the mouth portion, the screw cover being constructed with an inner skirt having an outer annular bead which is so constructed that in the fully tightened position of the screw cover the bead is in sealing engagement with the zone of the mouth portion having the smaller inner diameter, while in a partly unscrewed position of the cover the bead engages only the inwardly protruding, axially extending projections in the zone of the mouth portion having the greater inner diameter.

When the screw cover of the cultivation container according to the invention is partly screwed off, the outer annular bead of the inner skirt will be moved from a position in which it sealingly engages the zone of the mouth portion having the smaller inner diameter into the zone where the axially extending projections are arranged, and a communication is thereby established between the interior of the container and the surrounding air through passages formed between successive axially extending projections, the outer bead and the inner face of the mouth portion between successive projections. The cross sectional area of each of these passages is determined, for a given outer diameter of the annular bead, by the inner diameter of the mouth portion in the zone where the axially extending projections are arranged.

The length of the axially extending projections and the pitch of the screw thread of the screw cover determine the limits within which the screw cover can be turned while maintaining a constant cross sectional area of the passages between successive axially extending projections, and these factors can be so adapted that a well defined passage area can be obtained, even if the angle of turning varies within wide limits.

For reasons of production the axially extending projections, of which, e.g., six may be provided, are preferably constructed with plane inner faces.

It is observed that the axially extending projections may have a larger extension in the circumferential direction of the mouth portion than the intervening spaces, in which case the latter will assume the character of recesses in a zone of the mouth portion having the same inner diameter as the remaining zone of the mouth portion.

DESCRIPTION OF THE PREFERRED EMBODIMENT

Figure 1:
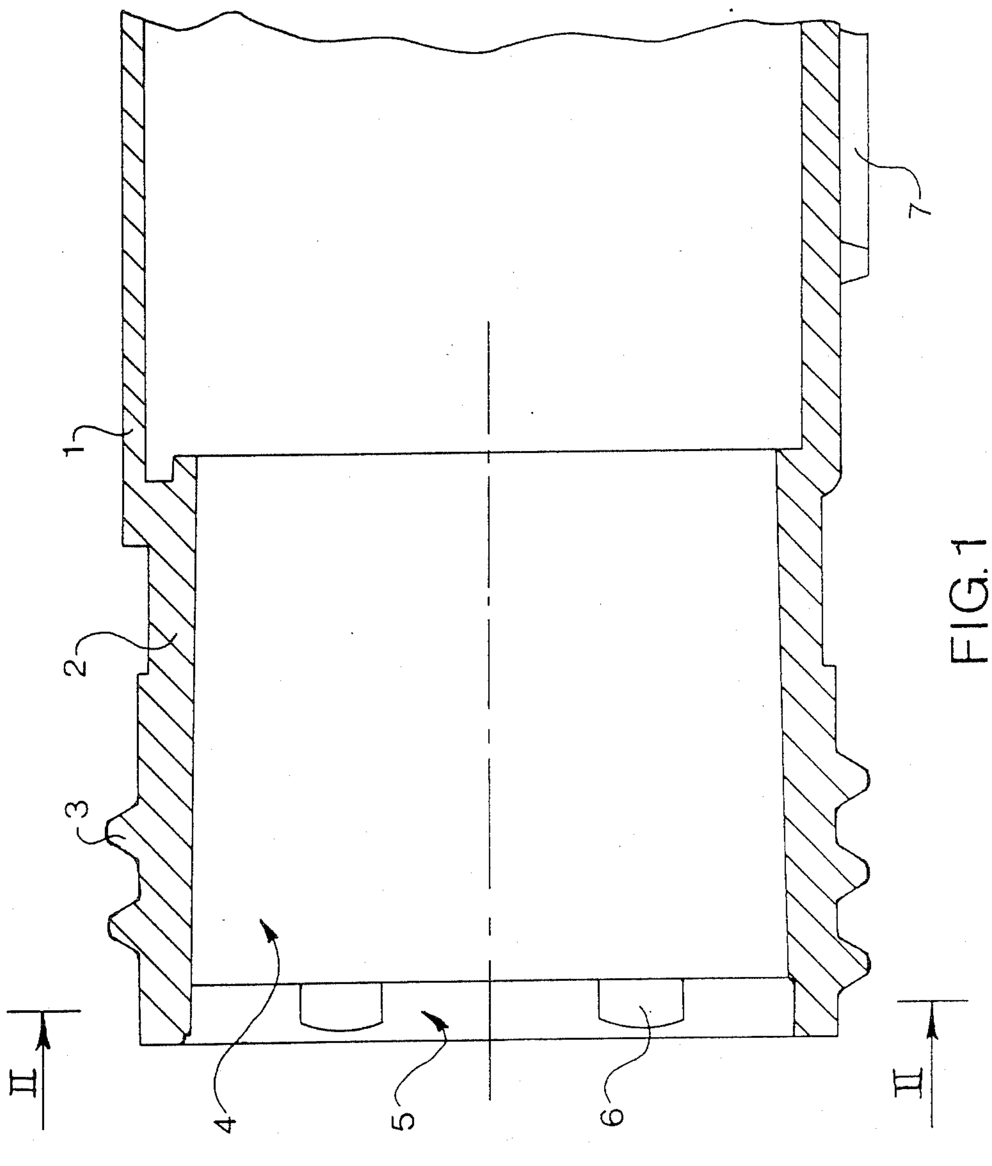
FIG. 1 shows a longitudinal section along the line I—I in FIG. 2 through the mouth portion of a cell cultivation container according to an embodiment of the invention, the screw cover being removed.
Figure 2:
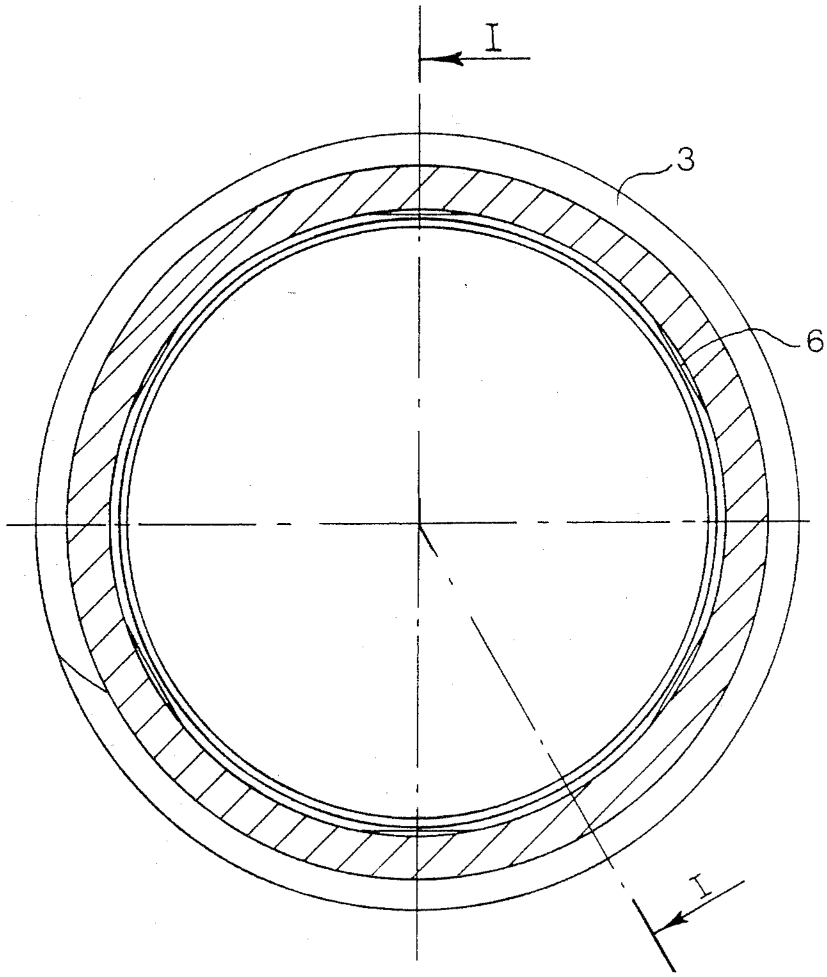
FIG. 2 shows a cross section of the mouth portion along the line II—II in FIG. 1.

The cultivation container shown in FIGS. 1 and 2 consists of a container portion 1 and a mouth portion 2, the latter being provided with an outer screw thread 3 and being constructed interiorly with two zones of different diameter, viz. a zone 4 having a smaller diameter and a zone 5 having a greater diameter, the zone 5 being situated adjacent the edge of the mouth. In the zone 5 six equi-distant inwardly protruding and axially extending projections 6 having plane inner faces are provided.

At its bottom side the container portion 1 is constructed with some ribs 7 to keep the container portion raised above the supporting surface.

Figure 3:
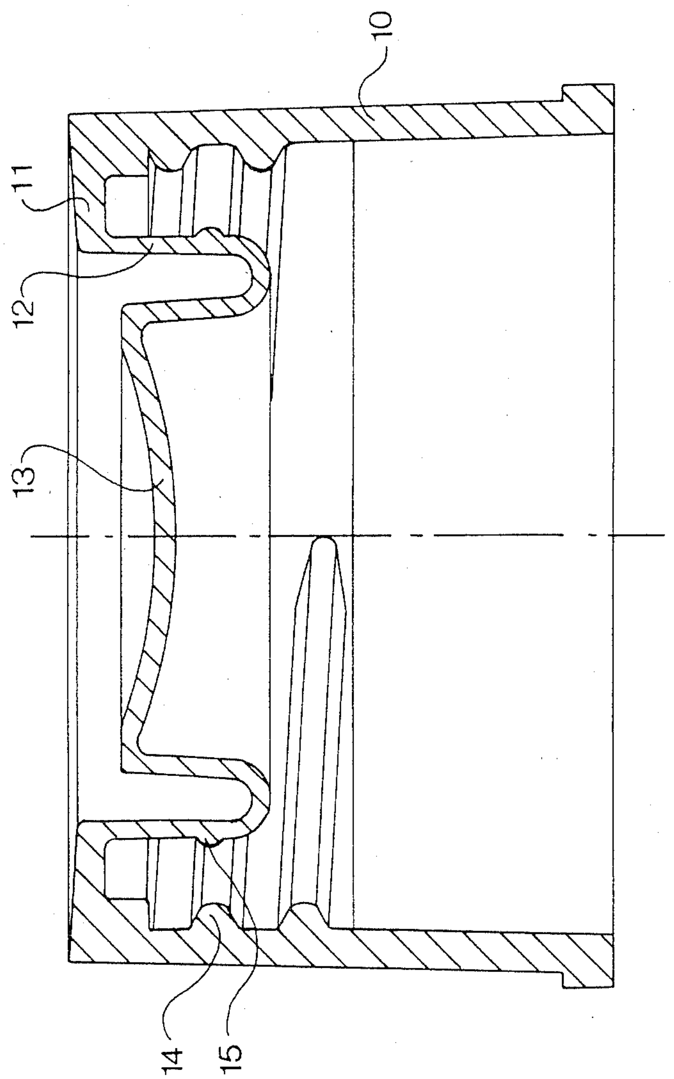
FIG. 3 shows a longitudinal section through a screw cover for the cultivation container of FIGS. 1 and 2.

The screw cover shown in FIG. 3 comprises an outer skirt 10, which via a connecting piece 11 is connected with an inner U-shaped skirt 12. The screw cover also has a dish-shaped central portion 13. On the inner side of the outer skirt 10 a screw thread 14 is provided for engagement with the outer screw thread 3 of the mouth portion 2 of FIGS. 1 and 2. On the outer side of the U-shaped inner skirt 12 an annular bead 15 is provided.

When the screw cover of FIG. 3 is fully screwed onto the mouth portion 2 of FIGS. 1 and 2, the bead 15 will be present in the zone 4 and will be in sealing engagement with the inner side of the mouth portion in this zone 4.

When the screw cover is partly screwed off, the bead 15 moves towards the edge of the mouth and reaches the zone 5. In this zone the bead will only be in contact with the plane faces of the projections 6 and thereby passages having a well defined cross-sectional area are formed in the intervals between the projections 6. This well defined cross-sectional area will be maintained when the screw cover is turned more or less away from the closing position, as long as the bead 15 is kept within a zone corresponding to the axial length of the projections 6. When the angle of turning is kept within an interval corresponding to the axial length of the projections, a well defined venting of the cultivation container and/or a well defined introduction of surrounding air into the container can therefore be obtained.

Both the container as such and the screw cover are preferably made from a plastic material.

We claim:

1. A cell cultivation device whose interior can be sealed with respect to exposure to the surrounding atmosphere or exposed to the surrounding atmosphere via a predetermined cross sectional area, said container device comprising a container element which comprises a container portion defining the interior of said container element and a cylindrical neck portion which terminates in a mouth, said cylindrical neck portion defining an axis therethrough and providing a first zone adjacent to the mouth thereof and a second zone located between the first zone and the container portion, the neck portion along said first zone defining a larger inner diameter than the neck portion along said second zone, said container element also including at least two axially extending projections connected to the neck portion along said first zone so as to extend inwardly of said neck portion, and a screw cover element for attachment to the cylindrical neck portion of said container element, said screw element defining an inner skirt with an outer annular bead, said screw cover element being dimensioned such that when fully tightened over the neck portion of said container element, said outer annular bead will be in sealing engagement with the neck portion of said container element along said second zone of said neck portion, while when in a partially unscrewed position said outer annular bead will engage only the inwardly protruding, axially extending projections connected to the neck portion along said first zone, such that a predetermined cross sectional area for exposure of the interior of said container element and the surrounding atmosphere is provided by said projections between the inner skirt of said screw cover element and the neck portion of said container element along said first zone to which said projections are attached.

2. The cell cultivation container device as defined in claim 1 wherein each of the projections connected to the neck portion of said container element along said first zone has an inner surface which faces the axis of said neck portion, each said inner face being planar.

* * * * *